United States Patent
Wang et al.

(10) Patent No.: US 10,859,587 B2
(45) Date of Patent: Dec. 8, 2020

(54) APPLICATION OF ARTIFICIALLY EXPRESSED HSP27 PROTEIN IN DETECTING A RESIDUE OF A β2-ADRENERGIC RECEPTOR AGONIST-BASED DRUG

(71) Applicants: HENAN ACADEMY OF AGRICULTURAL SCIENCE, Henan (CN); Fangyu Wang, Henan (CN)

(72) Inventors: Fangyu Wang, Henan (CN); Ruiguang Deng, Henan (CN); Gaiping Zhang, Henan (CN); Xiaofei Hu, Henan (CN); Jing Wang, Henan (CN); Qingxia Lu, Henan (CN); Guangxu Xing, Henan (CN); Qiuying Yu, Henan (CN); Jun Luo, Henan (CN); Junfang Hao, Henan (CN); Dong Zhao, Henan (CN); Jifei Yang, Henan (CN)

(73) Assignee: HENAN ACADEMY OF AGRICULTURAL SCIENCE, Henan (CN)

( * ) Notice: Subject to any disclaimer, the term of this patent is extended or adjusted under 35 U.S.C. 154(b) by 0 days.

(21) Appl. No.: 16/349,846

(22) PCT Filed: Dec. 12, 2016

(86) PCT No.: PCT/CN2016/109503
§ 371 (c)(1),
(2) Date: May 14, 2019

(87) PCT Pub. No.: WO2018/090413
PCT Pub. Date: May 24, 2018

(65) Prior Publication Data
US 2019/0277867 A1    Sep. 12, 2019

(30) Foreign Application Priority Data

Nov. 15, 2016 (CN) .................. 2016 1 10017690

(51) Int. Cl.
*G01N 33/94* (2006.01)
*C07K 14/47* (2006.01)

(52) U.S. Cl.
CPC ......... *G01N 33/9433* (2013.01); *C07K 14/47* (2013.01); *G01N 2500/04* (2013.01)

(58) Field of Classification Search
CPC .............. G01N 33/15; G01N 33/9433; G01N 2500/04; C07K 14/47
See application file for complete search history.

(56) References Cited

PUBLICATIONS

International Search Report from International Application No. PCT/CN2016/109503 dated Aug. 8, 2017.
Danyi, et al., "Solubilisation and binding characteristics of a recombinant β2-adrenergic receptor expressed in the membrane of *Escherichia coli* for the multianalyte detection of β-agonists and antagonists residues in food-producing animals", Science Direct, Analytica Chimica Acta 589, 2007, pp. 159-165.
Imura, et al., "Differential Expression of Small Heat Shock Proteins in Reactive Astrocytes after Focal Ischemia: Possible Role of β-Adrenergic Receptor", The Journal of Neuroscience, 19(22), Nov. 15, 1999, pp. 9768-9779.
Lv, et al., "Research Progress in Methods for Detecting Clenbnterol", 2014, pp. 10-12 and 55.
Rojanathammanee, et al., "The 27-kDa Heat Shock Protein Confers Cytoprotective Effects through a β2-Adrenergic Receptor Agonist-Initiated Complex with β-Arrestin", G Protein-Coupled Receptor Regulation of Apoptosis, vol. 75, No. 4, 2009, pp. 855-865.
Somara, et al., "Tropomyosin interacts with phosphorylated HSP27 in agonist-induced contraction of smooth muscle", Am J Physiol Cell Physiol, 286, Jan. 28, 2004, pp. C1290-C1301.
Zhang, et al., "Spectroscopic Studies on the Interaction Between Clenbuteral and Bovine Serum Albumin Using MCR-ALS Approach", Journal of Nanchang University (Natural Science), vol. 34, No. 2, Apr. 2010, pp. 150-155.

*Primary Examiner* — Robert S Landsman
(74) *Attorney, Agent, or Firm* — Dorsey & Whitney LLP

(57) ABSTRACT

Provided is an application of an artificially expressed HSP27 protein in detecting β2-adrenergic receptor stimulant drug residue.

8 Claims, 1 Drawing Sheet

US 10,859,587 B2

APPLICATION OF ARTIFICIALLY EXPRESSED HSP27 PROTEIN IN DETECTING A RESIDUE OF A β2-ADRENERGIC RECEPTOR AGONIST-BASED DRUG

TECHNICAL FIELD

The invention belongs to the field of drug residue detection, and particularly relates to the application of an artificially expressed HSP27 protein in detecting residue of a β2-adrenergic receptor agonist based drug.

BACKGROUND ART

β2-adrenergic receptor agonists, also known as β2-agonists, are a class of chemically synthesized derivatives of phenethylamines, usually preserved in the form of hydrochlorides, and the common β2-adrenergic receptor agonists include clenbuterol hydrochloride, brombuterol, salbutamol, ractopamine, mabuterol hydrochloride and the like. Since a β2-adrenergic receptor agonist can promote growth of muscle tissue, reduce fat deposition, improve meat quality, and improve feed conversion rate in animal, they have been widely used as feed additives in livestock and poultry production since the 1980s. The mechanism for increasing lean meat production is to stimulate the synthesis of adenylate cyclase by adrenoceptor, thereby increasing the concentration of cyclic adenosine monophosphate (c AMP) to increase activity of hormone-sensitive lipase and accelerate fat decomposition. Additionally, a β2-adrenergic receptor agonist can reduce the concentration of $Mg^{2+}$ in the blood, indirectly promote muscle excitability, and inhibit protein decomposition and fat synthesis, thereby increasing synthesis of muscle proteins. A person who eats lean pork, viscera and processed products thereof containing clenbuterol hydrochloride will be poisoned, with typical symptoms including muscle tremor, palpitations, nervousness, headache, dizziness, nausea, vomiting, tremble and the like, and in severe cases, death may occur. At present, the rapid detection method of β2-adrenergic receptor agonist, either ELISA or gold-labeled test strip method, is based on immunology and established by the specific action between an antigen and an antibody. β2-AR (adrenergic receptor) is a member of the G protein-coupled receptor (GPCR) superfamily. As a typical GPCR, its physiological functions such as structural function, regulation mechanism, signal transduction and the like have been deeply studied. A G protein-coupled receptor can be expressed as protein in all expression systems of *Escherichia coli*, yeast, baculovirus and mammals, and has certain functional activity, which varies depending on the type of receptor and the characteristics of the host cell.

Molecular Docking is a method for studying the interaction between small drug molecules and protein receptor macromolecules, is mutual recognition between ligand and receptor in essence, and involves spatial variation and energy changes of molecules, which is one of the important methods in the design of drug molecules.

Heat Shock Proteins (HSP), also known as Heat Stress Proteins (HSP) or Stress Proteins (SP), are a group of highly conserved proteins that are efficiently expressed by cell or organisms under the induction by stress sources, such as the conditions of high temperature, hypoxia, oxidative stress, infection, hunger, trauma, metabolism and the like, and are widely distributed in various organisms. HSP27 is an important member of the HSP subfamily with a molecular weight of 15 to 30 ku (low molecular weight heat shock protein), and it mainly participates in the stabilization of microfilaments and cytokine signal transduction, protects cells from damage caused by various stress factors and the like. At present, there is no report on the ability of HSP27 to detect a β2-adrenergic receptor agonist based drug.

SUMMARY OF THE INVENTION

With the aid of molecular docking technology, the present invention finally obtains a new detection method of β2-adrenergic receptor agonist based drugs, which uses the specific binding of an artificially expressed HSP27 protein to a β2-adrenergic receptor agonist based drug. The HSP27 protein is artificially synthesized and purified, followed by ELISA binding experiments, and the results show that the artificially synthesized protein has good binding ability with a β2-adrenergic receptor agonist based drug, which further verifies the feasibility of molecular docking technology. The protein of the present invention can be applied to the qualitative and quantitative detection of a β2-adrenergic receptor agonist based drug.

In order to achieve the above object, the present invention adopts the following technical solutions:

Use of an artificially expressed HSP27 protein in detecting residue of a β2-adrenergic receptor agonist based drug.

The artificially expressed HSP27 protein can specifically bind to a β2-adrenergic receptor agonist based drug.

The use of the artificially expressed HSP27 protein comprises any artificial expression mode for the artificially expressed HSP27 protein with the protein as a core, including but not limited to protein expression by a prokaryotic expression system, a eukaryotic expression system and a yeast expression system.

The artificially expressed HSP27 protein is used for the detection of a β2-adrenergic receptor agonist based drug, including but not limited to an enzyme-linked immunosorbent assay.

The artificially expressed HSP27 protein is used in the quantitative and qualitative detection of a β2-adrenergic receptor agonist based drug.

The artificially expressed HSP27 protein can specifically bind to a β2-adrenergic receptor agonist based drug, and can be prepared into a detection kit, a test strip or a test card for β2-adrenergic receptor agonist based drug.

The beneficial effects of the present invention are as follows:

(1) In the present invention, with the aid of the molecular docking technology, ELISA screening using an expressed and purified HSP27 was performed, and the resulting protein could specifically bind to a β2-adrenergic receptor agonist based drug. The results show that the artificially synthesized HSP27 protein can bind well with a β2-adrenergic receptor agonist based drug.

(2) Since there are many types of β2-adrenergic receptor agonist based drugs, and it is difficult to obtain antibody against such drugs, the HSP27 protein obtained by the present invention can avoid this problem efficiently, the protein can be quickly obtained by an artificial synthesis method, and further the detection cost is very low.

(3) The artificially synthesized protein of the present invention has a high yield with a good purification effect, and a high specific binding with the drug.

(4) The HSP27 protein obtained by the present invention has a simple expression process that is easy to operate; and the drug residue can be rapidly, qualitatively and quantitatively detected by labeling the drug.

SPECIFIC MODES FOR CARRYING OUT THE EMBODIMENTS

Figure 1:
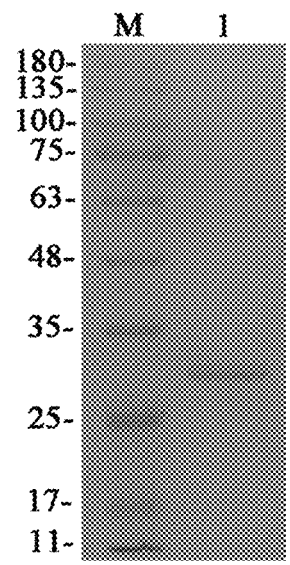
FIG. 1 shows the results of SDS-PAGE identification of the purified HSP27 protein. In the figure, M is a broad-spectrum 180 KD protein Marker, and 1 is a purified HSP27 protein.

Specific embodiments of the present invention will be further described in detail below with reference to the Examples.

Example 1: Small Molecule Docking Technology

1. Preparation for Docking

The molecular structure of the small molecule β2-adrenergic receptor agonist required for docking was downloaded from ZINC, and its structure was optimized to obtain its energy-minimized state for subsequent docking.

The proteins were β2 adrenergic receptor protein 2RH1 and heat shock protein 27 (HSP27) 3ROR, both of them were downloaded from the PDB database, the corresponding ligands and non-essential parts were removed, and hydrogenation and energy minimization were performed.

According to the literature, the 2RH1 docking pocket was set as the region including Asp113, Asn312, Ser203, Phe193, Phe289, Phe290, Val114, Val117, Trp109, Tyr308, Tyr316, Tyr199, Trp286 and Thr118 residues, Threshold was defined as 0.50, Bloat was defined as 10A.

According to the specific conditions of 3ROR, the docking pocket was set as the region including Glu99, Asp65, Arg209, Phe100, Tyr50, Cys103, Asp203, Tyr202, Ser200, Asn199, Glu198, Trp62, Met66, Met67, Val98 and Ser45 residues and the like, Threshold was defined as 0.50, Bloat was defined as 10A.

2. Molecular Docking

The above-mentioned region for protein docking was used as a receptor, a small molecule was used as a ligand, the FlexX method was used for docking work, and the docking conditions were set based on the default condition in SYBYL. The Total_Score value in the docking results was used as the final criterion. The docking results of the same small molecule for two proteins were shown in Table 1.

TABLE 1

Results of docking between β2-adrenergic receptor agonist based drug and proteins

| β2-adrenergic receptor agonist based drug | CAS | Total_Score HSP27 | β2- adrenergic receptor protein |
|---|---|---|---|
| Dobutamine (Dobutamine hydrochloride) | 34368-04-2 (49745-95-1) | 8.4035 | 7.5982 |

TABLE 1-continued

Results of docking between β2-adrenergic receptor agonist based drug and proteins

| β2-adrenergic receptor agonist based drug | CAS | Total_Score HSP27 | β2- adrenergic receptor protein |
|---|---|---|---|
| Fenoterol | 13392-18-2 | 7.8134 | 7.3290 |
| Ractopamine | 97825-25-7 | 7.0472 | 6.8865 |
| Salbutamol | 18559-94-9 | 6.3827 | 5.7219 |
| Pirbuterol | 38677-81-5 | 6.3238 | 5.5702 |
| Terbutaline | 23031-25-6 | 6.2437 | 5.7557 |
| Mabatero | 56341-08-3 | 6.0874 | 5.0646 |
| Metaproterenol | 586-06-1 | 5.8220 | 5.8766 |
| Clenbuterol | 129138-58-5 | 5.8202 | 4.5850 |
| Brombuterol | 41937-02-4 | 5.7717 | 4.5829 |
| Isoproterenol | 7683-59-2 | 5.4242 | 5.8632 |
| Cimaterol | 54239-37-1 | 5.4104 | 5.2559 |
| Adrenaline | 51-43-4 | 5.2629 | 5.4472 |
| Clorprenaline | 3811-25-4 | 4.7317 | 5.1257 |
| Phenylethanolamine | 7568-93-6 | 4.2296 | 4.6572 |

3. Analysis of Docking Results

The analysis of docking results showed that the docking results between β2-adrenergic receptor agonist based drug and HSP27 were mostly higher than those between β2-adrenergic receptor agonist based drug and β2-adrenergic receptor, indicating that the β2-adrenergic receptor agonist based drug has better binding ability to HSP27.

Example 2: HSP27 Protein Expression Experiment

According to the HSP27 gene sequence published in GenBank, the corresponding primers were designed to amplify the sequence of the CDS region, the resultant sequence was enzyme-digested and ligated to a pLSLa vector, which was subjected to PCR identification and sequencing, then transformed into BL21 (DE3) host bacteria, and subjected to induced expression by adding IPTG. The target protein was purified by an agarose resin column, and the characteristics of the expressed and purified protein were identified by SDS-PAGE (see FIG. 1 for the results). The results in FIG. 1 show that, the artificially synthesized protein of the present invention has a high yield with good purification effect.

Example 3: Identification of HSP27 Protein

The artificially expressed HSP27 protein at an optimal concentration was selected as a coating antigen, and coated on the ELISA plate in an amount of 50 μL/well. The plate was placed in a 37° C. constant temperature incubator for reaction for 2 h, washed with PBST for 4 times, and air-dried at room temperature. BSA with a mass fraction of 1% was added as a blocking solution in amount of 200 μL/well, and reaction was carried out at a constant temperature of 37° C. for 1 h. The resultant plate was washed with PBST for 4 times, and air-dried at room temperature. Then, HSP27 polyclonal antiserum with gradient concentrations was added at 50 μL/well, a negative control (NC) was set, and the plate was held at 37° C. for 30 min, and washed for 4 times. 50 μL of goat anti-mouse secondary antibody (1:1000) was added to each well, and the plate was held at 37° C. for 30 min, and then washed for 4 times. The color development reaction was carried out with TMB color developing solution in an amount of 100 μL/well, and 10 minutes later, the reaction was terminated with 50 μL of 2 mol/L $H_2SO_4$. The absorbance of each well was read at 450 nm with a microplate reader.

TABLE 2

ELISA identification results of artificially expressed HSP27 protein

| Protein concentration of HSP27 | Serum dilution ratio | | | | | | | | | |
|---|---|---|---|---|---|---|---|---|---|---|
| | 5000 | 10000 | 20000 | 40000 | 80000 | 160000 | 320000 | 640000 | 1280000 | 2560000 |
| 1 μg/mL | 4.00 | 3.92 | 4.00 | 3.77 | 3.50 | 2.60 | 1.63 | 0.97 | 0.67 | 0.51 |

Example 4: Binding Experiment Between HSP27 Protein and Small Molecules

1. The bacteria solution of BL21 (DE3) host bacteria of artificially expressed HSP27 was subjected to ultrasonication, and then coated in gradient on a ELISA plate with an initial concentration of 100 μg/mL (based on the protein) in an amount of 50 μL/well;

2. 100 ng/mL of small molecules conjugated biotin was added into the resultant ELISA plate in an amount of 50 μL/well, mixed well on a shaker, and incubated at 37° C. for 30 min in the dark; the ELISA plate was washed with an ELISA plate washing machine for 4 times, or the liquid in the wells of the ELISA plate was manually removed by shaking out, each well was filled with diluted buffer solution, and then shaken out the liquid to dry again, and washing as repeated in this way for 4 times;

3. HRP-labeled streptavidin conjugate was added into the ELISA plate, and the reaction was carried out at 37° C. for 30 min; washing was performed in the same way as the above step for 4 times.

Figure 2:
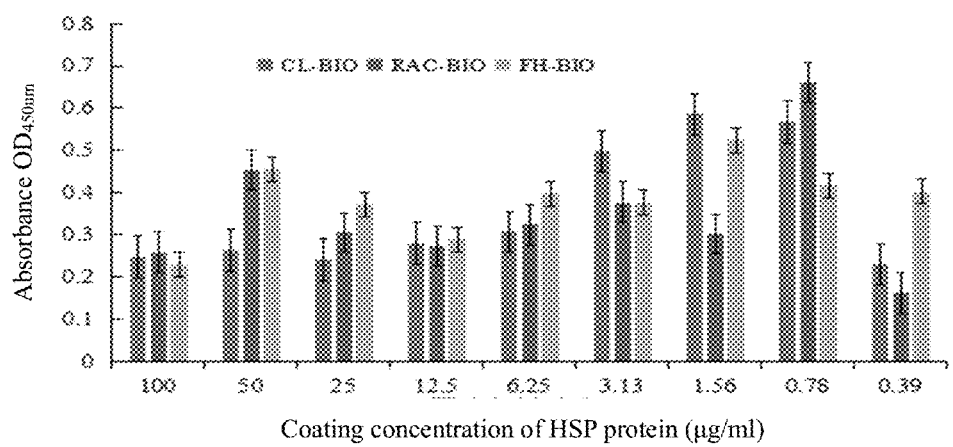
FIG. 2 shows the results of the ELISA reaction of the purified HSP27 protein and small molecules. In the figure, the abscissa represents different coating concentrations of HSP protein, and the ordinate represents OD value; the columns corresponding to coating concentrations of each HSP protein listed from left to right are CL-BIO, RAC-BIO, FH-BIO (BIO represents biotin).

4. TMB solution was added into corresponding microwells according to the required amount of 100 μL per well, and the plate was shaken on the ELISA plate shaker for 30 s, and subjected to color development at room temperature for 10 min;

5. 50 μL of 2 mol/L sulfuric acid was added to each well to terminate the reaction, and the plate was shaken on the ELISA plate shaker for 30 s, and then the absorbance at 450 nm of each well was read with a microplate reader, and the results were judged (see FIG. 2 for the results).

The results in FIG. 2 indicate that adrenergic receptor agonists such as small molecule FH (fenoterol), CL (Clenbuterol) and RAC (ractopamine) and the like can bind to HSP27; HSP27 can play a role of binding to adrenergic receptor agonist in vitro, which lays the foundation for the detection of adrenergic receptor agonist by HSP.

What is claimed is:

1. A method for detecting a residue of a β2-adrenergic receptor agonist-based drug, comprising: specifically binding an artificially expressed HSP27 protein to the β2-adrenergic receptor agonist-based drug; wherein the β2-adrenergic receptor agonist-based drug is one or more selected from dobutamine, fenoterol, ractopamine, salbutamol, pirbuterol, terbutaline, mabatero, clenbuterol, brombuterol and cimaterol.

2. The method according to claim 1, wherein the artificially expressed HSP27 protein is expressed by a prokaryotic expression system, a eukaryotic expression system or a yeast expression system.

3. The method according to claim 1, wherein the specific binding of the artificially expressed HSP27 protein to a β2-adrenergic receptor agonist-based drug is performed by an enzyme-linked immunosorbent assay.

4. The method according to claim 1, comprising specifically binding the artificially expressed HSP27 protein to the β2-adrenergic receptor agonist-based drug, and then the absorbance at 450 nm of the resultant is read with a microplate reader so as to quantitatively and qualitatively detect a β2-adrenergic receptor agonist-based drug.

5. A method for preparing a detection kit for β2-adrenergic receptor agonist-based drug, comprising preparing an artificially expressed HSP27 protein that can specifically bind to a β2-adrenergic receptor agonist-based drug.

6. A method for preparing a test device for identifying a β2-adrenergic receptor agonist-based drug, comprising preparing an artificially expressed HSP27 protein that can specifically bind to a β2-adrenergic receptor agonist-based drug.

7. The method of claim 6, wherein the device is a test strip.

8. The method of claim 6, wherein the device is a test card.

* * * * *